United States Patent [19]

Jäger

[11] 4,073,817
[45] Feb. 14, 1978

[54] PROCESS FOR THE MANUFACTURE OF PERFLUOROALKYL IODIDE-OLEFINE ADDUCTS

[75] Inventor: Horst Jäger, Bettingen, Switzerland

[73] Assignee: Ciba-Geigy AG, Basel, Switzerland

[21] Appl. No.: 528,621

[22] Filed: Dec. 2, 1974

Related U.S. Application Data

[63] Continuation-in-part of Ser. No. 172,574, Aug. 17, 1971, abandoned.

[30] Foreign Application Priority Data

Aug. 24, 1970 Switzerland .................. 12590/70

[51] Int. Cl.$^2$ ............................................. C07C 17/28
[52] U.S. Cl. ...................... 260/653.1 T; 260/340.9 R; 260/348.18; 560/205; 260/614 A; 260/614 F; 260/633; 260/669 R; 260/648 F
[58] Field of Search ................ 260/658.1 T, 653.1 T

[56] References Cited

U.S. PATENT DOCUMENTS

| | | | |
|---|---|---|---|
| 2,906,781 | 9/1959 | Montgomery | 260/651 R |
| 3,213,149 | 10/1965 | Takahashi et al. | 260/651 R |
| 3,454,657 | 7/1969 | Decker et al. | 260/653.1 T |
| 3,557,224 | 1/1971 | Jaeger | 260/653.1 T |
| 3,631,115 | 12/1971 | Nakagawa et al. | 260/653.1 T |

FOREIGN PATENT DOCUMENTS

| | | | |
|---|---|---|---|
| 920,855 | 3/1963 | United Kingdom | 260/6.58 C |

*Primary Examiner*—C. Davis
*Attorney, Agent, or Firm*—Edward McC. Roberts; Prabodh I. Almaula

[57] ABSTRACT

A process for the manufacture of perfluoroalkyl iodide adducts is provided, wherein a perfluoroalkyl iodide is reacted with an olefine in the presence of an amine and a metal salt of groups Ia to IVa or Ib to VIIIb of the periodic system, the amine and metal salt optionally being in the form of an amine-metal salt complex. The end product optionally may be deiodized. The adducts may be used as intermediates for the manufacture of products used for finishing textiles, paper or leather and other solids, especially for rendering such substrates oleophobic or hydrophobic.

19 Claims, No Drawings

PROCESS FOR THE MANUFACTURE OF PERFLUOROALKYL IODIDE-OLEFINE ADDUCTS

RELATED APPLICATION

This application is a continuation in part of copending application Ser. No. 172,574, filed Aug. 17, 1971 now abandoned.

The subject of the invention is a process for the manufacture of perfluoroalkyl iodide-olefine adducts which possess a perfluoroalkyl radical with 6 to 24 carbon atoms and an optionally substituted aliphatic or cycloaliphatic radical with at most 12 carbon atoms, characterised in that (a) at least one perfluoroalkyl iodide with 6 to 24 carbon atoms is reacted with (b) at least one optionally substituted linear or cyclic olefine which contains at most 12 carbon atoms, in the presence of (c) at least one amine and (d) at least one metal salt of a metal of Groups Ia to IVa or Ib to VIIIb of the periodic system, optionally in the form of an amine-metal salt complex, at 0 to 350° C and 0 to 200 atmospheres gauge, and the product is deiodised if required.

The ratios of the quantities of the components (a), (b), (c) and (d) vary within rather wide limits, depending on the reactivity of the individual components and on the intended properties of the end products. The preferred procedure is that 1 mol of the component (a) is reacted with 1 to 10 moles of the component (b) in the presence of 0.05 to 10 mols of the component (c) and 0.003 to 20 mols of the component (d).

The perfluoroalkyl iodides to be used according to the invention can be either in the form of monoiodides or in the form of diiodides. These perfluoroalkyl iodides of the component (a) are preferably branched or unbranched perfluoroalkyl iodides with 6 to 18, especially 6 to 14, carbon atoms.

As the component (b), alkenes optionally substituted by functional groups and containing 2 to 6 carbon atoms, or at most olefines which contain 6 to 12 carbon atoms, or an optionally substituted styrene, are preferably used.

The functional groups which are optionally present as substituents of the component (b) are, for example, hydroxyl, halogen, epoxide, ester or amide groups. The substituents of the styrene can, for example, be halogen, alkyl, alkoxy or hydroxyl; in particular, methylstyrene may also be mentioned. All components (b) contain at least 2 hydrogen atoms in the olefinic double bond.

Amongst the alkenes which can be used as component (b), ethylene or propylene are particularly suitable. Alkenes substituted by functional groups are, for example, allyl alcohol and also vinyl chloride, vinylidene chloride, vinyl fluoride, vinylidene fluoride, vinyl acetate and 1,2-dichloroethene; esters, for example lower alkyl esters, and amides of acrylic, methacrylic, crotonic, maleic, fumaric or itaconic acid, and in particular allyl formate and allyl acetate, diallyl fumarate and diallyl itaconate and divinyl fumarate and divinyl itaconate. Further, appropriate epoxides, for example of the formula

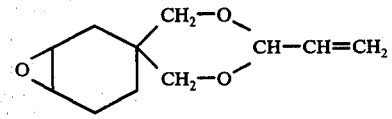

(1)

are also suitable. Cyclic olefines of particular interest correspond, for example, to the formula

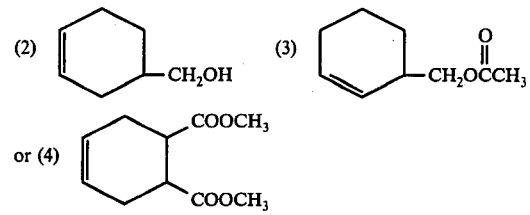

The adducts obtained according to the invention are frequently isomer mixtures, in that the perfluoroalkyl radical can add onto either the α- or the β-carbon atom of the ethylenically unsaturated bond of the olefine. For reasons of simplicity, only one isomer form is mostly mentioned in the present instance.

The amines which can be used as component (c) are especially primary, secondary or tertiary aliphatic, heterocyclic or aromatic amines. Amines which contain at least one oxygen atom in the molecule are preferred. Amines which contain at least one hydroxyl group in the molecule are here particularly suitable. Amines which are capable of assuming an amphoteric configuration, such as the alkanolamines, are of particular interest. Such alkanolamines preferably contain 2 to 6 carbon atoms.

The following amines may, for example, be mentioned individually: N-ethylethanolamine, aminoethylisopropanolamine, diethylethanolamine, N-(2-hydroxyethyl)-ethylenediamine, isopropanolamine, triisopropanolamine, N-ethylethanolamine and N-methylethanolamine, and in particular diethanolamine, triethanolamine and preferably monoethanolamine. Furthermore, amines such as N-hydroxyethylmorpholine, morpholine, N-hydroxyethylpiperazine, 3-diethylamino-phenol, glycine or diethylamine can also be used.

Amongst the metal salts to be used according to the invention as component (d), metal salts of a metal of Groups Ib to VIIIb, especially of the 4th to 6th period of the periodic system, are above all suitable. Metal salts of metals of Groups Ib and IIb are at the same time particularly suitable, such as, for example, cuprous, silver, gold, zinc, cadmium or mercury salts. Other preferred metal salts are derived from metals of Groups IIIb or VIIIb, especially of the 4th or 5th period, or from metals of Groups IVb or Vb, especially of the 4th to 6th period of the periodic system. These are yttrium, titanium, zirconium, niobium, tantalum, manganese, iron, ruthenium or rhodium salts.

Representatives of metals of Group Ia are, for example, sodium and potassium and of Group IIa are, for example, magnesium, calcium, strontium or barium. The metals of Group IIIa include gallium, thallium and indium and of Group IVa include germanium, tin or lead.

All references to the periodic system are references to the periodic system according to Mendelejeff. In various systems the present groups VIIIa and VIIIb correspond to groups 0 and VIII respectively.

The halides, such as the bromides, iodides or preferably chlorides, of the appropriate metals have proved particularly advantageous. Additionally, however, appropriate phosphates, carbonates, nitrates, sulphates, cyanides, hydride, acetylacetonates or alcoholates, for example ethylates or methylates, can also be used. Salt mixtures can also be used, including mixtures of salts of metals of different valency.

Cuprous chloride has proved particularly suitable.

The components (c) and (d) are preferably employed as amine-metal salt complexes, to which an excess of the complex-forming amine can be added as a solvent. At the same time it is also possible for the amine-metal salt complex to contain an excess of unreacted metal salt.

To facilitate isolation and re-use of the amine-metal salt complex, binders and absorbents can also be conjointly used as carriers for the catalyst complex. Aluminum oxide, silicon dioxide, charcoal, kieselguhr or natural and synthetic molecular sieves are, for example, suitable for this purpose.

The reaction of the components (a) and (b) preferably takes place at 60° to 250° C or especially at 120° to 180° C.

Depending on whether the boiling points of the components (a), (b) and (c) are below or above 60° C, the reaction is appropriately carried out in an autoclave or in a non-pressure apparatus, at atmospheric pressure. In the autoclave, a pressure becomes established which depends on the initially introduced amounts of the components (a) and (b). The pressures lie in the range of 1–200 atmospheres gauge, preferably at 1 to 160 atmospheres gauge, depending on the components undergoing the reaction. The reaction can be carried out continuously or batchwise.

The reaction takes place smoothly. In each case, mixtures of products of perfluoroalkyl iodides are obtained, mainly consisting of 1:1 adducts.

The reaction can be carried out in the absence or presence of a solvent. Suitable solvents are, for example, fluorinated alkanes, fluorinated halogenoalkanes, alcohols, ethers, aromatic hydrocarbons or cycloaliphatic compounds.

The perfluoroalkyl iodide-olefine adducts possessing functional groups are valuable intermediate products which can be used for the synthesis of products used for practical applications, for example for imparting oleophobic and hydrophobic properties.

By splitting off iodine by hydrogenation, or by splitting off hydrogen iodide, perfluoroalkylalkenes and perfluoroalkanes are obtained from the iodides. The perfluoroalkylalkenes can be converted into alkanes by subsequent hydrogenation. The following reaction routes may be mentioned as a possible selection:

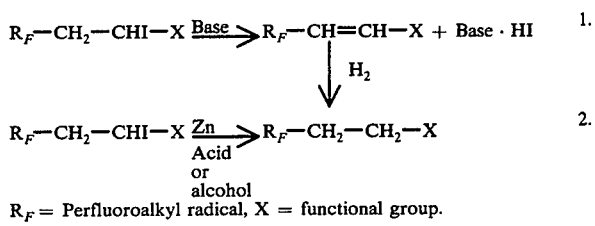

$R_F$ = Perfluoroalkyl radical, X = functional group.

In some cases, the splitting off of hydrogen iodide already occurs during the reaction of the perfluoroalkyl iodides with the olefine. The resulting products then contain a double bond.

The reactive functional groups X can be hydroxyl, halogen, epoxide, ester or amide groups.

After esterification of the hydroxyl group with acrylic, methacrylic, crotonic, itaconic, fumaric or maleic acid or with, for example, allyl isocyanate, reactive esters or carbanates are produced, which can be polymerised.

Reaction of an amine group with an acid chloride of the abovementioned acids yields a reactive amide which can be polymerised.

Carboxyl groups can be reacted to give vinyl esters. Epoxides can be used directly, or are reacted with the above unsaturated acids to give reactive esters which can in turn again be polymerised. Amides can be crosslinked as such or as methylolamides with aminoplasts.

The products for practical application manufactured from the intermediate products described above are very suitable for finishing textiles, paper and leather and also other solids, for example wood, metals or glass, but especially for rendering such substrates oleophobic or hydrophobic.

EXAMPLE 1

500 g of a perfluoroalkyl iodide telomer consisting of 30% of n-perfluorohexyl iodide, 46% of n-perfluorooctyl iodide, 20.5% of n-perfluorodecyl iodide + $C_4$, $C_{12}$ and $C_{14}$ perfluoroalkyl iodides, together with 1 g of $Cu^I$ Cl and 5 g of ethanolamine are introduced into a 1 liter stainless steel autoclave. An excess of ethylene is then injected. The autoclave is heated to 140° C over the course of 45 minutes and is kept at this temperature for 45 minutes. Shortly before reaching the reaction temperature, the pressure in the autoclave already begins to drop from 138 atmospheres gauge to 130 atmospheres gauge and remains constant thereat after 30 minutes.

530 g of solid white waxy substance are recovered from the autoclave and distilled in vacuo. Hereupon a total fracton of 484 g (boiling point 29 to 150° C/5 mm Hg) of a semi-solid white substance are isolated.

22 g of starting material are isolated from the cooled trap. Analyses by gas chromatography and mass spectrography yield the following result:

| | | |
|---|---|---|
| M 474 = $CF_3(CF_2)_5CH_2CH_2I$ | 36% | |
| M 574 = $CF_3(CF_2)_7CH_2CH_2I$ | 34.5% | |
| M 674 = $CF_3(CF_2)_9CH_2CH_2I$ | 9.8% | |
| M 502 = $CF_3(CF_2)_5(CH_2)_4I$ | 8.2% | |
| M 602 = $CF_3(CF_2)_7(CH_2)_4I$ | 8.7% | |
| M 702 = $CF_3(CF_2)_9(CH_2)_4I$ | 2.0% | + impurities |

M = molecular weight.

Relative to converted starting material ($\overline{M}$ = 546), the yield of perfluoroalkylalkyl iodide ($\overline{M}$ = 574), calculated for the batch, is 484/502.74 = 96.41% of theory.

EXAMPLE 2

500 g of a perfluoroalkyl iodide telomer consisting of 30% of n-perfluorohexyl iodide, 46% of n-perfluorooctyl iodide, 20.5% of n-perfluorodecyl iodide + $C_4$, $C_{12}$ and $C_{14}$ perfluoroalkyl iodides together with 1 g of $Cu^I$ Cl and 5 g of ethanolamine are introduced into a 1 liter stainless steel autoclave. An excess of propylene is then injected. The autoclave is heated to 140° C over the course of 45 minutes and left at this temperature for 45 minutes. As the reaction temperature is reached, the pressure drops over the course of 20 minutes from 20 atmospheres gauge to 15 atmospheres gauge and remains constant for the remaining duration of the reaction.

509 g of light brown, viscose substance are recovered from the autoclave and distilled in vacuo. Hereupon a total fraction of 460 g (boiling point 33° to 150° C/10 mm Hg) of fluid-solid, white substance is isolated.

33 g of starting material are isolated from the cooled trap. Analyses by gas chromatography and mass spectrography yield the following results:

| | |
|---|---|
| M 488 = CF$_3$(CF$_2$)$_5$—CH$_2$—CH(CH$_3$)—I | 40% |
| M 588 = CF$_3$(CF$_2$)$_7$—CH$_2$—CH(CH$_3$)—I | 51.3% |
| M 688 = CF$_3$(CF$_2$)$_9$—CH$_2$—CH(CH$_3$)—I | 8.7% |

Relative to converted starting material ($\overline{M}$ = 546), the yield of perfluoroalkyl iodide ($\overline{M}$ = 588), calculated for the batch, is 460/502.74 = 96.27% of theory.

EXAMPLE 3

54.6 g of a perfluoroalkyl iodide telomer consisting of 30% of n-perfluorohexyl iodide, 46% of n-perfluorooctyl iodide, 20.5% of n-perfluorodecyl iodide + C$_4$, C$_{12}$ and C$_{14}$ perfluoroalkyl iodides and 11.2 g of Δ$^3$-tetrahydrobenzyl alcohol are introduced into a 3000 ml stainless steel autoclave. 100 mg of Cu$^I$Cl and 1 g of ethanolamine are used as the catalyst. The reaction mixture is heated to 100° C, whereupon a reaction temperature of 150° to 160° C rapidly becomes established. The reaction mixture is kept at this temperature for 90 minutes. The pressure is 2 atmospheres gauge. After cooling the autoclave, 64 g of dark brown liquid substance are obtained. This crude product is dissolved in 250 ml of diethyl ether, the solution is washed three times with 50 ml of water and dried with sodium sulphate, and the ether is distilled off. A vacuum distillation of 58 g of purified substance gives the following:

| | Amount in g | Pressure mm Hg | Boiling point in ° C | Gas chromatogram |
|---|---|---|---|---|
| Cooled trap | 11 | | | Starting material |
| Fraction 1 | 21 | 40–3 | 40–60 | Starting material + 40% reaction products |
| Fraction 2 | 13.7 | 3 | 65–70 | Reaction products |
| Residue | 4.3 | Discarded | | |
| Total | 50.0 | | | |

By recording a mass spectrum of Fraction 2, compounds of the formula

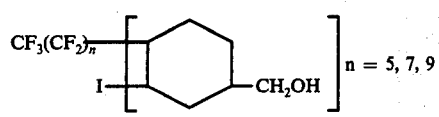

(101)

are identified by their "parent peaks" M = 558, 658 and 758.

The yield of the above compounds from Fractions 1 + 2 of the reaction described is 22.1/65.8 = 33.5% of theory relative to an average molecular weight of 658.

Elimination of HI from the above compounds 13.2 g of distillate (boiling point 65° to 70° C, 3 mm Hg) are treated with 50 ml of 50% strength potassium hydroxide solution in a 100 ml round flask and a steam distillation is started immediately. Hereupon 6.6 g of a clear, colourless substance are obtained, having a boiling point of 45° to 100° C/12 mm Hg after distillation. The following compounds are identified by recording a mass spectrum:

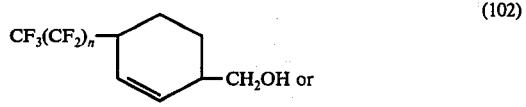

(102)

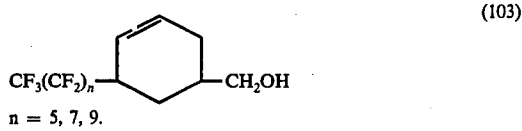

(103)

n = 5, 7, 9.

Relative to an average molecular weight of the starting material of 658 and an average molecular weight of the end product of 530, the yield is 66% of theory.

EXAMPLE 4

54.6 g of a perfluoroalkyl iodide telomer consisting of 30% of n-perfluoroalkyl iodide, 46% of n-perfluorooctyl iodide, 20.5% of n-perfluorodecyl iodide + C$_4$, C$_{12}$ and C$_{14}$ perfluoroalkyl iodides, together with 48 g of an epoxide of the formula

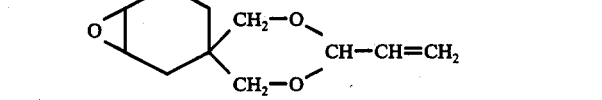

(104)

are introduced into a 300 ml stainless steel autoclave. 100 ml of Cu$^I$Cl and 1 g of triethanolamine are used as the catalyst. The reaction mixture is kept at 140° to 158° C for 135 minutes and is then discharged. Pressure 1 atmosphere gauge. 97 g of brown crude product are dissolved in 250 ml of ether, the solution is washed three times with 50 ml of water until neutral and dried with sodium sulphate, and the ether is distilled off. Yield: 95 g = 93% of theory. Calculated with regard to a compound of the formula

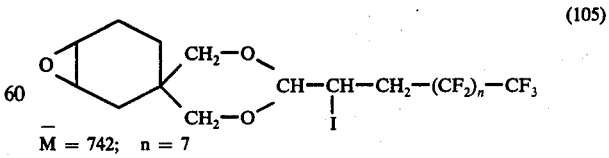

(105)

$\overline{M}$ = 742; n = 7 the epoxide content is 100%.

Recording a mass spectrum shows M + H = 643, 743, 843, M − H = 641, 741, 841, and a corresponding decomposition series, starting with M − I, = 515, 615, 715.

EXAMPLE 5

54.6 g of a perfluoroalkyl iodide telomer consisting of 30% of n-perfluorohexyl iodide, 46% of n-perfluorooctyl iodide, 20.5% of n-perfluorodecyl iodide + $C_4$, $C_{12}$ and $C_{14}$ perfluoroalkyl iodides, and 5.8 g of allyl alcohol are introduced into a 300 ml stainless steel autoclave. 100 mg of $Cu^ICl$ and 1 g of ethanolamine are used as the catalyst.

The reaction mixture is heated to 100° C, whereupon a reaction temperature of 140° to 155° C rapidly becomes established. This temperature is maintained for 120 minutes. The pressure is 2 atmospheres gauge. After cooling the autoclave, 50 g of brown viscous substance are discharged. This substance is distilled in vacuo.

| Cooled trap | 17 g | Starting material |
|---|---|---|
| Fraction I | 29 g | 2 mm Hg, 40 to 100° C Reaction product |

According to a mass spectrum of Fraction 1, compounds of the formula

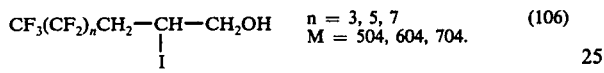
$$n = 3, 5, 7 \quad M = 504, 604, 704.$$ (106)

are obtained. The yield is 29/60.4 = 48.0% with regard to an average molecular weight of 604.

Elimination of HI from the above compounds:

a. 26 g of distillate (boiling point 40° to 110° C, 2 mm Hg) are treated with 50 ml of 50% strength potassium hydroxide solution in a 100 ml round flask and a steam distillation is started immediately.

Hereupon, 12.7 g of a clear yellow liquid are isolated, which after distillation boils at 38 to 93° C/15 mm Hg. The following compounds are identified by recording a mass spectrum: (107) $CF_3(CF_2)_n$—CH=CH—$CH_2OH$ n = 5, 7, 9; M = 376, 476, 576. The yield is 12.2/20.4 = 62.25% of theory with regard to an average molecular weight of 476.

b. The procedure described under (a) is followed, but instead of the 50% strength potassium hydroxide solution 30 g of pulverulent potassium hydroxide in 100 ml of epichlorohydrin are employed. During the reaction, which lasts 5 hours, the water is removed azeotropically. An epoxide of the formula

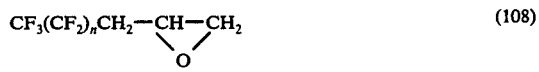 (108)

n = 5, 7, 9 is obtained. Yield 71.5%; epoxide content 93.7% of theory.

EXAMPLE 6

55 g of a compound of the formula

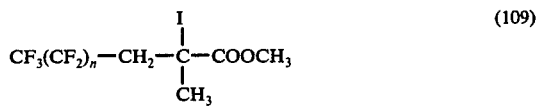 (109)

wherein n is 5, 7, 9, are dissolved in a mixture of 100 ml of ethyl acetate and 20 ml of glacial acetic acid.

6 g of zinc dust are added to this solution and HCl gas is passed in for 5 minutes at the rate of 20 bubbles/minute. The reaction mixture is kept for 5 hours at the reflux temperature and is then cooled and filtered, and the solution is concentrated. The residue is distilled in a high vacuum and yields 18.6 g of a cream-coloured substance. Melting point 167° - 204° C/0.1 mm Hg. The yield is 42% of theory.

Recording a mass spectrum (M 420, 520, 620) confirms the following structure

 (110)

n = 5, 7, 9.

The above ester can be converted into the free acid by saponification.

Further esters are manufactured in accordance with the above example, for instance

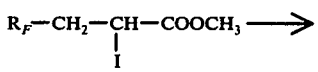

(111)

(112)

(113)

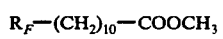

(114)

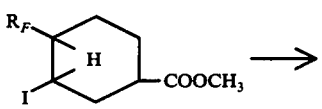

(115)

(116)

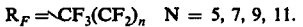

$R_F = CF_3(CF_2)_n$ N = 5, 7, 9, 11.

EXAMPLES 7 TO 72

The table which follows summarises the experimental conditions for carrying out Examples 7 to 72 and the results obtained. The calculation of the effective yield is shown for the case of Example 7.

In each case 150 g (0.3 mol = 100%) of a perfluoroalkyl iodide telomer consisting of 23.5% of n-perfluorohexyl iodide (M = 446), 44.9% of n-perfluorooctyl iodide (M = 546), 26.1% of n-perfluorodecyl iodide (M = 646), 2.0% of n-perfluorododecyl iodide (M = 746) + further perfluoro compound are reacted with 68 g (0.6 mol = 200%) of 1-octent in accordance with Example 1. 36.04 g of 1-octent (107%), 5 g of the perfluoroalkyl iodide (3.4%) and 141.25 g of reaction product are obtained.

The product is identified by gas chromatography and mass spectrum.

The effective yield from 145 g (150 - 5) of the perfluoroalkyl iodide is:

141.25/177.48 = 79.58%

177.48 g is the theoretical yield at 100% conversion. The yields are calculated for an average molecular weight of the perfluoroalkyl iodide of 546.

The amount of the perfluoroalkyl iodide employed is always 96.6% and the percentages of the olefines employed are indicated in each case.

In the table the symbols furthermore have the following meaning:
EA = ethanolamine
DEA = diethanolamine
TEA = triethanolamine
$Al_2O_3$ = aluminum oxide for chromatography
$SiO_2$ = silica gel for use for distribution chromatography or kieselguhr or molecular sieve
$R_f$ = perfluoroalkyl radical
Me = metal.

| Ex. | Reaction time (minutes) | t° C | p atms. gauge | Catalyst Amine | Me salts | Carrier | Starting material $CF_3(CF_2)_nI$ n=5,7,9,11 recovered | Olefine employed 1-octene | End product (% yield) |
|---|---|---|---|---|---|---|---|---|---|
| 7 | 240 | 160 | 1 | EA 1 g | Cu$^I$Cl 0.5 g | $Al_2O_3$ 2 g | 3.4% | 200% | $CF_3(CF_2)_n$—CH—CH(CH$_2$)$_5$CH$_3$ \| I  79.58% |

| Ex. | Reaction time (minutes) | t° C | p atms. gauge | Catalyst Amine | Me salts | Carrier | Starting material $CF_3(CF_2)_nI$ n=5,7,9,11 recovered | Olefine employed (cyclohexyl-CH$_2$OC(O)CH$_3$) | End products (% yield) ($R_F$—, I— cyclohexenyl—CH$_2$OCCH$_3$) |
|---|---|---|---|---|---|---|---|---|---|
| 8 | 180 | 140 | 1 | EA 1 g | Cu$^I$Cl 0.2 g | — | 50.32% | 110% | 82.31% |
| 9 | 120 | 140 | 1 | Piperidine 0.2 g | SnCl$_2$ 0.4 g | $Al_2O_3$ 0.5 g | 61.28% | 100% | 26.74% |
| 10 | 120 | 160 | 1 | TEA 1.0 g | Nb$^{IV}$ methylate 0.5 g | — | 42.02% | 100% | 87.20% |
| 11 | 240 | 140 | 1 | Triethylamine 1.0 g | FeCl$_3$ 0.3 g | SiO$_2$ 1.5 g | 72.15% | 50% | 48.23% |

| Ex. | Reaction time (minutes) | t° C | p atms. gauge | Catalyst Amine | Me salts | Carrier | Starting material $CF_3(CF_2)_nI$ n=5,7,9,11 recovered | Olefine employed $CH_2=C-C-OCH_3$ \| \|\| CH$_3$ O | End products (% yield) $R_f$—, I— CH$_3$ \|  —C—COOCH$_3$ \| CH$_2$ |
|---|---|---|---|---|---|---|---|---|---|
| 12 | 240 | 160 | 1 | EA 0.5 g | Cu$^I$Cl 0.2 g | $Al_2O_3$ 1.0 g | 79.45% | 100% | 66.0% |
| 13 | 360 | 140 | 1 | EA 0.5 g | TiCl$_4$ 0.5 g | $Al_2O_3$ 2.0 g | 73.54% | 100% | 32.0% |
| 14 | 120 | 180 | 1 | Piperidine 0.4 g | SnCl$_2$ 0.4 g | $Al_2O_3$ 1.0 g | 52.31% | 100% | 98.5% |
| 15 | 240 | 160 | 1 | Triethylamine 1 g | FeCl$_3$ 1 g | $Al_2O_3$ 2 g | 56.85% | 50% | 77.5% |

| Ex. | Reaction time (minutes) | t° C | p atms. gauge | Catalyst Amine | Me salts | Carrier | Starting material $CF_3(CF_2)_nI$ n=5,7,9,11 recovered | Olefine employed $CH_2=CHCOOCH_3$ | End product (% yield) $R_f$—, I— CH—COOCH$_3$ \| CH$_2$ |
|---|---|---|---|---|---|---|---|---|---|
| 16 | 240 | 160 | 2 | EA 0.5 g | Cu$^I$Cl 0.2 g | $Al_2O_3$ 1.0 g | 81.52% | 110% | 80.5% |
| 17 | 240 | 140 | 3 | TEA 0.4 g | CdSO$_4$ 0.4 g | SiO$_2$ 1.0 g | 73.20% | 60% | 36.4% |
| 18 | 240 | 160 | 5 | Triethylamine 1 g | FeCl$_3$ 1 g | $Al_2O_3$ 2 g | 56.65% | 60% | 70% |
| 19 | 360 | 180 | 8 | EA 0.5 g | TiCl$_4$ 0.5 g | $Al_2O_3$ 2 g | 31.53% | 110% | 74.5% |
| 20 | 120 | 180 | 8 | Piperidine 0.4 g | SnCl$_2$ 0.4 g | $Al_2O_3$ 1.0 g | 30.20% | 110% | 76.5% |

| Ex. | Reaction time (minutes) | t° C | p atms. gauge | Amine | Catalyst Me salts | Carrier | Starting material $CF_3(CF_2)_nI$ n= 5,7,9,11 recovered | Olefine employed Dimethyl maleate | End product (% yield) $R_f$—[—C(H)—COOCH_3, —C(H)—COOCH_3] $I^-$ |
|---|---|---|---|---|---|---|---|---|---|
| 21 | 240 | 180 | 3 | EA 0.5 g | Cu$^I$Cl 0.2 g SnCl$_2$ 0.2 g | Al$_2$O$_3$ 1.0 g | 71.32% | 112% | 81.61% |
| 22 | 240 | 180 | 3 | EA 0.5 g | Cu$^I$Cl 0.2 g SnCl$_2$ 0.2 g | Al$_2$O$_3$ 1.0 g | 48.48% | Dimethyl itaconate 105% | $R_f$—CH$_2$—C(I)(COOCH$_3$)—CH$_2$COOCH$_3$ 91.12% |

| Ex. | Reaction time (minutes) | t° C | p atms. gauge | Amine | Catalyst Me salts | Carrier | Starting material $CF_3(CF_2)_nI$ n=5,7,9,11 recovered | Olefine Olefin employed (cyclohexene-CH$_2$OH) | End products (% yield) $R_f$–(cyclohexyl-I)–CH$_2$OH |
|---|---|---|---|---|---|---|---|---|---|
| 23 | 90 | 140 | 2 | Ethylamine 1 g | Cu$^I$Cl 0.1 g | — | 69% | 100% | 81.72% |
| 24 | 240 | 180 | 2 | TEA 0.5 g | CdSO$_4$ 0.5 g | — | 76.17% | 100% | 45.0% |
| 25 | 120 | 160 | 2 | EA 1.5 g | YCl$_3$ 0.5 g | — | 23.50% | 400% | 81.3% |
| 26 | 120 | 140 | 1 | DEA 0.4 g | AuCN 0.2 g | SiO$_2$ | 42.10% | 200% | 84.66% |

| Ex. | Reaction time (minutes) | t° C | p atms. gauge | Amine | Catalyst Me salts | Carrier | Starting material $CF_3(CF_2)_nI$ n=5,7,9,11 recovered | Olefine employed CH$_3$CH=CH$_2$ | End products (% yield) $CF_3(CF_2)_nCH_2$—CH(CH$_3$)I |
|---|---|---|---|---|---|---|---|---|---|
| 27 | 120 | 140 | 25 | DEA 0.2 g | AuCN 0.1 g | SiO$_2$ 0.3 g | 32.05% | 180% | 90.74% |
| 28 | 60 | 180 | 17 | TEA 0.4 g | GaCl$_3$ 0.2 g | SiO$_2$ 1.0 g | 39.67% | 115% | 90.00% |
| 29 | 120 | 160 | 31 | EA 0.3 g | YCl$_3$ 0.2 g | active charcoal 0.3 g | 16.98% | 180% | 91.53 |
| 30 | 60 | 180 | 20 | TEA 0.2 g | Cu$^I$Cl 0.1 g | Al$_2$O$_3$ 0.5 g | 30.45% | 115% | 92.05% |
| 31 | 180 | 140 | 20 | DEA 0.2 g | TiCl$_4$ 0.1 g | — | 32.75% | 115% | 92.70% |
| 32 | 360 | 140 | 20 | EA 5 g | Cu$^I$Cl 7 g | Al$_2$O$_3$ 10 g | 1.30% | 170% | 99.95% |

| Ex. | Reaction time (minutes) | T° C | p atms. gauge | Amine | Catalyst Me salts | Carrier | Starting material $CF_3(CF_2)_nI$ n=t°5,7,9,11 recovered | Olefine employed CH$_2$=CH$_2$ | End Products (% Yield) $R_fCH_2CH_2I$ |
|---|---|---|---|---|---|---|---|---|---|
| 33 | 90 | 120 | 43 | DEA 0.1 g | AuCN 0.1 g | SiO$_2$ 0.5 g | 74.60% | 290% | 97.9% |
| 34 | 60 | 140 | 43 | TEA 0.2 g | CdSO$_4$ 0.2 g | — | 10.38% | 290% | 99.0% |
| 35 | 90 | 160 | 12 | EA 0.3 g | CYCl$_3$ 0.2 g | Active charcoal | 66.49% | 115% | 97.67% |
| 36 | 160 | | 15 | Piperidine 0.5 g | SnCl$_4$ 0.2 g | Al$_2$O$_3$ 1.0 g | 64.50% | 150% | 97.16% |
| 37 | 90 | 100 | 12 | TEA 0.5 g | FeCl$_3$ 0.2 g | SiO$_2$ 1 g | 93.81% | 115% | 92.25% |
| 38 | 60 | 160 | 27 | EA 0.5 g | RuCl$_3$ 0.5 g | — Catalyst | 46.80% | 175% | 91.1% |
| 39 | 90 | 160 | 23 | Piperidine 2.0 g | KCN 1.5 g | SiO$_2$ 4.0 g | 42.90% | 115% | 93.97% |
| 40 | 60 | 160 | 23 | TEA 0.1 g | GaCl$_3$ 0.1 g | Al$_2$O$_3$ 0.5 g | 58.43% | 115% | 64.71% |
| 41 | 120 | 140 | 26 | EA 5 g | Cu$^I$Cl 5 g | Al$_2$O$_3$ 8 g | 0% | 130% | 98.0% |

| Ex. | Reaction time (minutes) | t° C | p atms. gauge | Amine | Catalyst Me salts | Carrier | Starting material $CF_3(CF_2)_nI$ N = 5,7,9,11 recovered | Olefine employed $CH_2=CH-CH_2COOCH_3$ | End products (% yield) $R_F-CH_2-\underset{I}{CH}COOCH_3$ |
|---|---|---|---|---|---|---|---|---|---|
| 42 | 240 | 145 | 1 | TEA 0.4 g | $CdSO_4$ 0.4 g | — | 73.94% | 60% | 78.3% |
| 43 | 360 | 140 | 1 | TEA 0.4 g | $GaCl_3$ 0.4 g | $SiO_2$ 1.0 g | 21.84% | 200% | 90.53% |
| 44 | 240 | 160 | 1 | Triethyl-amine 1 g | $FeCl_3$ 1 g | $Al_2O_3$ 2 g | 44.24% | 60% | 81.1% |
| 45 | 120 | 180 | 1 | Piperidine 0.4 g | $SnCl_2$ 0.4 g | $Al_2O_3$ 1.0 g | 14.63% | 110% | 90.6% |

| Ex. | Reaction time (minutes) | t° C | p atms. gauge | Amine | Catalyst Me salts | Carrier | Starting material $CF_3(CF_2)_nI$ n=5,7,9,11 recovered | Olefine employed $CH_3-CH=CH-COOCH_3$ | End products (% yield) $R_F-\underset{CH_3}{\overset{}{C}}H-\underset{I}{CH}-COOCH_3$ |
|---|---|---|---|---|---|---|---|---|---|
| 46 | 240 | 140 | 1 | EA 0.5 g | $Cu^ICl$ 0.5 g | $Al_2O_3$ 2.0 g | 90.61% | 110% | 55.21% |
| 47 | 120 | 180 | 1 | EA 1 g | $YCl_3$ 0.5 g | $SiO_2$ 2.0 g | 76.00% | 50% | 56.69% |
| 48 | 360 | 140 | 1 | DEA 0.5 g | $TiCl_4$ 0.5 g | — | 90.00% | 200% | 42.29% |
| 49 | 360 | 180 | 1 | EA 0.5 g | $RhCl_3$ 0.3 g | — | 73.70% | 110% | 51.0% |
| 50 | 120 | 160 | 1 | TEA 1 g | Nb butylate 0.5 g | — | 83.54% | 200% | 41.38% |
| 51 | 120 | 140 | 1 | TEA 1 g | Mn acetylacetonate | — | 80.75% | 200% | 59.05% |

| Ex. | Reaction time (minutes) | t° C | p atms. gauge | Amine | Catalyst Me salts | Carrier | Starting material $CF_3(CF_2)_nI$ n=5,7,9,11 recovered | Olefine employed $CH_2=CH_2$ | End products (% yield) $R_F-CH_2-CHCII +$ $R_F-CHCl-CH_2I$ |
|---|---|---|---|---|---|---|---|---|---|
| 52 | 300 | 140 | 14 | EA 0.5 g | $Cu^ICl$ 0.3 g | $Al_2O_3$ 1.0 g | 46.37% | 200% | 90.0% |
| 53 | 300 | 140 | 16 | EA 0.5 g | $Cu^ICl$ 0.3 g | $Al_2O_3$ 1.0 g | 49.35% | $CH_2=CHF$ 200% | $R-CH_2CHFI +$ $R-CHF-CH_2I$ 94.9% |
| 54 | 300 | 140 | 15 | EA 0.5 g | $Cu^ICl$ 0.3 g | $Al_2O_3$ 1.0 g | 54.30% | $CH_2=CF_2$ 200% | $RCH_2CF_2I +$ $RCF_2-CH_2I$ 91.1% |
| 55 | 300 | 140 | 9 | EA 0.5 g | $Cu^ICl$ 0.3 g | $Al_2O_3$ 1.0 g | 61.00% | $CH_2=CCl_2$ 200% | $RCH_2CCl_2I +$ $RCCl_2CH_2I$ 84.95% |

| Ex. | Reaction time (minutes) | t° C | p atms. gauge | Amine | Catalyst Me salts | Carrier | Starting material $CF_3(CF_2)_nI$ n=5,7,9,11 recovered | Olefine employed $Cl-CH=CHCl$ | End products (% yield) $R_F-CHCl-CHCII$ |
|---|---|---|---|---|---|---|---|---|---|
| 56 | 300 | 160 | 11 | EA 0.5 g | $Cu^ICl$ 0.3 g | $Al_2O_3$ 1.0 g | 85.45% | 220% | 62.39% |
| 57 | 300 | 180 | 16 | EA 1.0 g | $Cu^ICl$ 0.3 g $SnCl_2$ 0.3 g | $Al_2O_3$ 1.0 g | 80.00% | 220% | 57.89% |

| Ex. | Reaction time (minutes) | t° C | p atms. gauge | Amine | Catalyst Me salts | Carrier | Starting material $CF_3(CF_2)_nI$ n=5,7,9,11 recovered | Olefine employed cyclohexene-COOCH₃ | End products (% yield) $R'_F$, I, cyclohexyl-COOCH₃ |
|---|---|---|---|---|---|---|---|---|---|
| 58 | 360 | 140 | 1 | EA 1.0 g | $Cu^ICl$ 0.5 g | $Al_2O_3$ 1.5 g | 70.13% | 100% | 58.32% |
| 59 | 240 | 160 | 1 | Piperidine 0.6 g | $SnCl_2$ 0.2 g $SnCl_4$ 0.2 g | $Al_2O_3$ 1.0 g | 22.00% | 80% | 57.27% |
| 60 | 120 | 180 | 1 | EA 0.5 g | $TiCl_4$ 0.5 g | — | 22.90% | 100% | 69.6% |

-continued

End products (% yield)

$$\text{C}_6\text{H}_5\text{-CH(I)-CH}_2\text{-R}_F +$$

$$\text{C}_6\text{H}_5\text{-CH(R}_F\text{)-CH}_2\text{I}$$

Olefine employed: $\text{C}_6\text{H}_5\text{-CH=CH}_2$

| Ex. | Reaction time (minutes) | t° C | p atms. gauge | Amine | Catalyst Me salts | Carrier | Starting material $CF_3(CF_2)_nI$ n=5,7,9,11 recovered | Olefine employed | End products (% yield) |
|---|---|---|---|---|---|---|---|---|---|
| 61 | 240 | 160 | 1 | EA 1.0 g | Cu$^I$Cl 0.5 g | Al$_2$O$_3$ 2.0 g | 67.50% | 100% | 98.00% |
| 62 | 360 | 140 | 1 | EA 0.5 g | YCl$_3$ 0.5 g | Active charcoal 0.5 g | 81.34% | 200% | 76.66% |

End products (% yield): $R_F\text{-CH}_2\text{-CH(I)-(CH}_2)_8\text{-COOCH}_3$

| Ex. | Reaction time (minutes) | t° C | p atms. gauge | Amine | Catalyst Me salts | Carrier | Starting material $CF_3(CF_2)_nI$ n=5,7,9,11 recovered | Olefine employed $CH_2=CH-(CH_2)_8COOCH_3$ | End products (% yield) |
|---|---|---|---|---|---|---|---|---|---|
| 63 | 240 | 160 | 1 | Triethylamine 0.5 g | Cu$^I$Cl 0.2 g | Al$_2$O$_3$ 1.0 g | 5.78% | 100% | 86.17% |
| 64 | 360 | 140 | 1 | TEA 0.6 g | Nb$^V$ butylate 0.6 g | — | 24.88% | 100% | 98.67% |
| 65 | 360 | 180 | 1 | Piperidine 4.0 g | Mn acetylacetonate 0.5 g | SiO$_2$ 2.0 g | 2.00% | 100% | 95.1% |
| 66 | 120 | 180 | 1 | Piperidine 0.7 g | SnCl$_2$ SnCl$_4$ 0.7 g each | Al$_2$O$_3$ 0.7 g | — | 150% | 90.50% |

Olefine employed: $CH_2=CHCNHCH_2OH$ with $\|O$

End products (% yield): $R_F\text{-CH(I)-CH}_2\text{-CONHCH}_2OH$

| Ex. | Reaction time (minutes) | t° C | p atms. gauge | Amine | Catalyst Me salts | Carrier | Starting material $CF_3(CF_2)_nI$ n=5,7,9,11 recovered | Olefine employed | End products (% yield) |
|---|---|---|---|---|---|---|---|---|---|
| 67 | 120 | 180 | 1 | EA 0.5 g | SnCl$_2$ CuCl 0.2 g each | Al$_2$O$_3$ 1.0 g | 87.55% | 162% | 57.9% |

End products (% yield): $R_F\text{-CH}_2\text{-CH(I)-CH}_2OH$

Olefine employed: $CH_2=CHCH_2OH$

| Ex. | Reaction time (minutes) | t° C | p atms. gauge | Amine | Catalyst Me salts | Carrier | Starting material $CF_3(CF_2)_nI$ n=5,7,9,11 recovered | Olefine employed | End products (% yield) |
|---|---|---|---|---|---|---|---|---|---|
| 68 | 240 | 160 | 7 | TEA 0.5 g | Cu$^I$Cl 0.2 g | Al$_2$O$_3$ 1.0 g | 35.60% | 200% | 83% |
| 69 | 120 | 140 | 1 | TEA 0.6 g | CdSO$_4$ 0.4 g | — | 62.65% | 125% | 95.7% |
| 70 | 120 | 140 | 5 | DEA 0.5 g | TiCl$_4$ 0.2 g | — | 73.12% | 125% | 69.0 |
| 71 | 240 | 180 | 10 | EA 1.5 g | RuCl$_3$ 0.2 g | — | 73.12% | 400% | 26.0% |
| 72 | 240 | 160 | 10 | Piperidine 0.5 g | SnCl$_2$ 0.5 g SnCl$_4$ 0.5 g | Al$_2$O$_3$ 1 g | 20.85% | 400% | 80.3% |

End product 71 contains approx. 90% of $R_F\text{CH}_2\text{-CH}\underset{O}{\overset{}{\diagdown\diagup}}\text{CH}_2$ in the reaction product.

End product 72 contains approx. 5% of $R_F\text{CH}_2\text{-CH}\underset{O}{\overset{}{\diagdown\diagup}}\text{CH}_2$ in the reaction product.

In the last-mentioned experiments, the amine catalyst has eliminated HI from the adduct $R_F\text{CH}_2\text{-CH(I)-CH}_2OH$. The reaction yields to tarry by-products in addition to the epoxide isolated.

Example 73

| Reaction time (minutes) | t° C | P atms. gauge | Catalyst Amine | Catalyst Me salts | Catalyst Carrier | Starting material $C_7F_{15}I$ recovered | Olefine employed $CH_2=C(CH_3)(CH_3)$ | End product [1] (% effective yield) |
|---|---|---|---|---|---|---|---|---|
| 240 | 160 | 14 | EA 1.0 g | $Cu^lCl$ 0.5 g | $Al_2O_3$ 2.0 g | 0% | 200% | 94.24% |

[1] The analytical data of the end product show the following:
a) Mass spectrum compound $$C_7F_{15}CH=CH\diagdown^{CH_3}_{CH_3} \quad (M = 424)$$

b) Nuclear resonance spectrum:

$$C_7F_{15}CH=C\diagdown^{CH_3}_{CH_3}$$

$$C_7F_{15}\underset{|}{\overset{CH_3}{C}}=CH\atop CH_3$$

$$C_7F_{15}CH_2-\underset{I}{\overset{CH_3}{C}}\diagdown CH_3$$

c) Gas chromatogram: 75.9%  $C_7F_{15}CH=C\diagdown^{CH_3}_{CH_3}$ 19.6%  $C_7F_{15}\underset{|}{\overset{}{C}}=CH-CH_3 \atop CH_3$ 2.9%  $C_7F_{15}-CH_2-\underset{I}{\overset{CH_3}{C}}-CH_3$ + small proportions of further compounds.

The ethanolamine present in excess is, in this case, capable of eliminating hydrogen iodide from the resulting alkyl iodide in the reaction mixture, and of forming an alkene. The yield was therefore calculated with regard to 1-perfluoroheptyl-2-dimethyl-ethylene.

I claim:

1. Process for the manufacture of perfluoroalkyl iodide olefin adducts, which comprises reacting a) a linear or branched perfluoroalkyl mono- or di-iodide with 6 to 24 carbon atoms with b) a $C_2$-$C_{12}$ alkene or $C_2$-$C_{12}$ alkene substituted with a member selected from the group consisting of halogen a lower alkyl, wherein the carbon atoms of the olefinic double bond have at least two hydrogen atoms and wherein the alkene chain is linear or cyclic, in the presence of c) a basic primary, secondary or tertiary alkanol amine having 2 to 6 carbon atoms, and d) a halide, a sulphate, a cyanide, or an alcoholate of a metal of groups Ia to IVa or Ib to Vb and VIII of the periodic system, as catalyst pair, at 0° to 350° C and 0 to 200 atmospheres gauge.

2. Process according to claim 1, which comprises reacting (a) a linear or branched perfluoroalkyl mono- or di-iodide with 6 to 18 carbon atoms with b) an olefine selected from the group consisting of ethylene, propylene, vinyl chloride, vinylidene chloride, vinyl fluoride, vinylidene fluoride, and 1,2-dichloroethylene, in the presence of c) ethanolamine, diethanolamine, triethanolamine, N-methylethanolamine, N-ethylmethanolamine, diethylethanolamine or isopropanolamine and d) a member selected from the group consisting of halide, a sulphate, a cyanide, or an alcholate of a metal of groups Ia to IVa or Ib to Vb and VIII of the Periodic Table, as catalyst pair, at 0° to 350° C and 0 to 200 .

3. Process according to claim 1, wherein component (b) is an olefine selected from the group consisting of ethylene; propylene; vinyl chloride; vinylidene chloride; vinyl fluoride; vinylidene fluoride; and 1,2-dichloroethylene, component (c) is a primary, secondary or tertiary alkanolamine, and component (d) is a member selected from the group consisting of a halide, sulphate, cyanide, or alcoholate of the metal, the product being a 1:1 perfluoroalkyl iodide:olefine adduct.

4. Process according to claim 1, which comprises using as the component (a) branched or unlinear perfluoroalkyl monoiodides or perfluoroalkyl diiodides with 6 to 18 carbon atoms.

5. Process according to claim 1, wherein component ) is $C_2$-$C_6$ alkenes or $C_2$-$C_6$ alkenes substituted by functional groups of claim 1 or $C_6$-$C_{12}$ mono or bicyclic olefines substituted by the functional groups of claim 1.

6. Process according to claim 5, wherein that functional group of the component b) is halogen.

7. Process according to claim 1, wherein component b) is ethylene or propylene.

8. Process according to claim 1, wherein component c) is N-ethylethanolamine, aminoethylisopropanolamine, diethylethanolamine, N-(2-hydroxyethyl)-ethylenediamine, isopropanolamine, triisopropanolamine, N-ethylmethanolamine, N-methylethanolamine, monoethanolamine, diethanolamine or triethanolamine.

9. Process according to claim 1, wherein component c) is amine which contains one hydroxyl group in the molecule.

10. Process according to claim 1, wherein component c) is an alkanolamine.

11. Process according to claim 1, wherein component c) is an alkanolamine with at most 6 carbon atoms.

12. Process according to claim 1, wherein component (d) is a halide, sulphate, cyanide, or alcoholate.

13. Process according to claim 1, wherein component (d) is a metal halide.

14. Process according to claim 13, wherein component (d) is cuprous chloride.

15. Process according to claim 1, wherein components (c) and (d) are used in the form of an amine-metal salt complex.

16. Process according to claim 1, wherein a binder or adsorbent is conjointly used as a carrier material for the amine-metal salt complex.

17. Process according to claim 16, wherein the binder or adsorbent is aluminum oxide, silicon dioxide or charcoal.

18. Process according to claim 1, which comprises reacting 1 mol of the component (a) with 1 to 10 mols of the component (b) in the presence of 0.05 to 10 mols of the component (c) and 0.003 to 20 mols of the component d) on an aluminum oxide carrier.

19. Process according to claim 1, which comprises reacting (a) a perfluoroalkyl iodide with 6 to 12 carbon atoms with (b) ethylene, in the presence of (c) ethanolamine, and (d) cuprous chloride on an aluminum oxide carrier.

* * * * *

UNITED STATES PATENT OFFICE
CERTIFICATE OF CORRECTION

Patent No. 4,073,817  Dated February 14, 1978

Inventor(s) HORST JÄGER

It is certified that error appears in the above-identified patent and that said Letters Patent are hereby corrected as shown below:

Claim 1, column 17, line 54, change "a" to -- and --.

Claim 2, column 18, line 50, after "0 to 200" insert -- atmospheric gauge --.

Claim 5, column 18, line 65, before ")" insert -- b --.

Signed and Sealed this

Eighth Day of August 1978

[SEAL]

Attest:

RUTH C. MASON
Attesting Officer

DONALD W. BANNER
Commissioner of Patents and Trademarks